(12) United States Patent
Amelink et al.

(10) Patent No.: US 11,666,212 B2
(45) Date of Patent: Jun. 6, 2023

(54) QUANTITATIVE RETINAL IMAGING

(71) Applicant: Nederlandse Organisatie voor toegepast-natuurwetenschappelijk onderzoek TNO, The Hague (NL)

(72) Inventors: Arjen Amelink, Gouda (NL); Fokko Pieter Wieringa, Elst (NL); Michiel Peter Oderwald, Delft (NL)

(73) Assignee: Nederlandse Organisatie voor toegepast-nataurwetenschappelijk onderzoek TNO, The Hague (NL)

( * ) Notice: Subject to any disclaimer, the term of this patent is extended or adjusted under 35 U.S.C. 154(b) by 405 days.

(21) Appl. No.: 16/463,253

(22) PCT Filed: Nov. 24, 2017

(86) PCT No.: PCT/NL2017/050772
§ 371 (c)(1),
(2) Date: May 22, 2019

(87) PCT Pub. No.: WO2018/097723
PCT Pub. Date: May 31, 2018

(65) Prior Publication Data
US 2019/0290125 A1    Sep. 26, 2019

(30) Foreign Application Priority Data
Nov. 25, 2016  (EP) .................................... 16200795

(51) Int. Cl.
*A61B 3/12*      (2006.01)
*A61B 3/14*      (2006.01)

(52) U.S. Cl.
CPC . *A61B 3/12* (2013.01); *A61B 3/14* (2013.01)

(58) Field of Classification Search
CPC ........... A61B 3/12; A61B 3/14; A61B 3/1225; G01B 11/2513; G01B 11/2518; G01B 11/2536; G01J 3/2846; G06T 7/0012
(Continued)

(56) References Cited

U.S. PATENT DOCUMENTS 5,467,104 A    11/1995  Furness, III et al.
10,117,570 B2*  11/2018  Glynn ..................... A61B 3/10
(Continued)

FOREIGN PATENT DOCUMENTS

CA    2284299 A1    3/2001
CN   103969745 A    8/2014
(Continued)

OTHER PUBLICATIONS

McClatchy DM 3rd, Rizzo EJ, Wells WA, et al. Wide-field quantitative imaging of tissue microstructure using sub-diffuse spatial frequency domain imaging. Optica. 2016;3(6):613-621 (Year: 2016).*
(Continued)

*Primary Examiner* — Travis S Fissel
(74) *Attorney, Agent, or Firm* — Leydig, Voit & Mayer, Ltd.

(57) ABSTRACT

A method and system are proposed for imaging the retinal structure of an eye. A light source is provided and a repetitive pattern is projected on the retina by said hght source having illuminated and non-illuminated portions with a spatial frequency larger than 0.5 mm-1. For the illuminated and non-illuminated portions a fluorescence level is measured; and a fluorescence level is derived as a corrected value for illuminated and non-illuminated areas.

20 Claims, 2 Drawing Sheets

(58) Field of Classification Search
USPC .......................................... 351/205, 206, 178
See application file for complete search history.

(56) References Cited

U.S. PATENT DOCUMENTS

| | | | |
|---|---|---|---|
| 2006/0069552 A1 | 3/2006 | Spitler | |
| 2007/0091265 A1* | 4/2007 | Kardon | A61B 3/0058 351/206 |
| 2009/0270717 A1 | 10/2009 | Newman | |
| 2011/0196239 A1 | 8/2011 | Behrend et al. | |
| 2014/0333898 A1 | 11/2014 | Boate et al. | |
| 2016/0157723 A1* | 6/2016 | Kanick | A61B 5/0075 600/476 |
| 2016/0309068 A1* | 10/2016 | Nadeau | A61B 5/1455 |
| 2017/0164836 A1* | 6/2017 | Krishnaswamy | G01B 11/2513 |
| 2018/0321148 A1* | 11/2018 | Xu | G01N 21/4795 |

FOREIGN PATENT DOCUMENTS

| | | |
|---|---|---|
| JP | 2010085621 A | 4/2010 |
| NL | 1024082 C1 | 2/2005 |
| WO | WO 2011/012646 A2 | 2/2011 |
| WO | WO 2014/151877 A1 | 9/2014 |

OTHER PUBLICATIONS

Sibai et al., "Quantitative fluorescence imaging enabled by spatial frequency domain optical-property mapping in the sub-diffusive regime for surgical guidance," Proc. SPIE 9311, Molecular-Guided Surgery: Molecules, Devices, and Applications (Year: 2015).*

Cuccia et al., "Modulated Imaging: Quantitative Analysis and Tomography of Turbid Media in the Spatial-Frequency Domain," Optics Letters, vol. 30, No. 11, pp. 1354-1356 (Jun. 1, 2005).

Cuccia et al., "Quantitation and Mapping of Tissue Optical Properties Using Modulated Imaging," Journal of Biomedical Optics, vol. 14(2), 024012, pp. 1-13 (Mar./Apr. 2009).

Gruppetta et al., "Theoretical Study of Multispectral Structured Illumination for Depth Resolved Imaging of Non-Stationary Objects: Focus on Retinal Imaging," Biomedical Optics Express, vol. 2, No. 2, pp. 255-263 (Feb. 2011).

Chetty et al. "Structured Illumination Microscopy for in-vivo Human Retinal Imaging: A Theoretical Assessment," Optics Express, vol. 20, No. 23, pp. 25700-25710 (Nov. 5, 2012).

O'Sullivan et al., "Diffuse Optical Imaging Using Spatially and Temporally Modulated Light," Journal of Biomedical Optics, vol. 17(7), 071311, pp. 1-14 (Jul. 2012).

Vervandier et al., "Single Snapshot Imaging of Optical Properties," Biomedical Optics Express, vol. 4, No. 12, pp. 2938-2944 (Dec. 2013).

Kanick et al., "Sub-Diffusive Scattering Parameter Maps Recovered Using Wide-Field High-Frequency Structured Light Imaging," Biomedical Optics Express, vol. 5, No. 10, pp. 3376-3390 (Oct. 2014).

Vienola et al., "Parallel Line Scanning Ophthalmoscope for Retinal Imaging," Optics Letters, vol. 40, No. 22, pp. 5335-5338 (Nov. 15, 2015).

Nadeau et al., "Multifrequency Synthesis and Extraction Using Square Wave Projection Patterns for Quantitative Tissue Imaging," Journal of Biomedical Optics, vol. 20(11), 116005, pp. 1-10 (Nov. 2015).

Roorda, HHS Public Access, PMCID: PMC2911957, "Applications of Adaptive Optics Scanning laser Ophthalmoscopy," http://www.ncbi.nlm.nih.gov/pmc/articles/PMC2911957/ (Apr. 1, 2011).

Zawadzki et al., "Adaptive-Optics SLO Imaging Combined with Widefield OCT and SLO Enables Precise 3D Localization of Fluorescent Cells in the Mouse Retina," OSA Publishing, Biomedical Optics Express, vol. 6, Issue 6, pp. 2191-2210 (2015).

Merino et al., "Adaptive Optics Enhanced Simultaneous *en-face* Optical Coherence Tomography and Scanning Laser Ophthalmoscopy," Optics Express, vol. 14, No. 8, pp. 3345-3353 (Apr. 17, 2006).

Gray et al., "In vivo Fluorescence Imaging of Primate Retinal Ganglion Cells and Retinal Pigment Epithelial Cells," Optics Express, vol. 14, No. 16, pp. 7144-7158 (Aug. 7, 2006).

Jian et al., "Wavefront Sensorless Adaptive Optics Optical Coherence Tomography for in vivo Retinal Imaging in Mice," Optics Express, vol. 5, No. 2, pp. 547-559 (Feb. 1, 2014).

European Patent Office, International Search Report in corresponding International Application No. PCT/NL2017/050772, dated Feb. 22, 2018 (3 pages).

McClatchy III et al., "Wide-Field Quantitative Imaging of Tissue Microstructure Using Sub-Diffuse Spatial Frequency Domain Imaging," Optica, vol. 3, No. 6, pp. 613-621 (Jun. 2016).

European Patent Office, Examination Report in corresponding European Patent Application No. 178172623 dated Apr. 14, 2022 (5 pages).

* cited by examiner

QUANTITATIVE RETINAL IMAGING

CROSS-REFERENCE TO RELATED APPLICATIONS

This patent application is a U.S. National Phase of PCT International Application No. PCT/NL2017/050772, filed Nov. 24, 2017, which claims priority to European Application No. 162007959, filed Nov. 25, 2016, which are both expressly incorporated by reference in their entireties, including any references contained therein.

FIELD

The invention relates to a method of obtaining an image of the human retina for the purpose of analysing tissue structure, function and biochemistry.

BACKGROUND

In the prior art, fundus imaging is a technique for obtaining high resolution images of the interior of the eye, in particular, the human retina. This can be done for many diagnostic reasons, e.g. to identify glaucoma, diabetic retinopathy, and age related macula degeneration. Fundus imaging can be performed with high resolution fundus cameras in multispectral images. Another technique is scanning laser ophthalmoscopy. Here, the retina is scanned by a point or line source, that is imaged on a photodiode or line camera. Since the only light that is received is directly related to the imaged point itself, diffraction and scattering is minimal and the resolution of the images is high. This technique can be applied for many different wavelengths, and can be combined with fluorescence measurements. However, the technique is cumbersome and expensive. Another technique is optical coherence tomography, wherein a reflected beam is optically combined with an incoming scanning point source beam, and scattering behaviour can be made visible. 2D high resolution cross sections can be produced, inter alia, to visualize structures in the retina, such as cysts, ruptures, or determining the retinal nerve fibre layer thickness. Angiography is another application area of optical coherence tomography. Multiple images can be used to distinguish differences attributed to blood flow. In this way blood vessels can be analysed. Although the eye is primarily imaged for studying the function of the eye itself, the prior art has also mentioned studies, e.g. wherein the vessel diameter is correlated to e.g. a risk of a myocardial infarct in patients. Also fluorescence markers can be used to label individual substances. In relation to this studies were performed to image beta amyloid aggregates in the retina. These aggregates are associated with Alzheimer's disease, and it is contemplated that the optical nerve system is physically closely linked to the brain.

While these techniques are promising, there is a problem in providing quantitative data on these images. For example, there is a problem on how to relate the fluorescence in quantitative sense to the aggregates.

A technique to optically measure tissue structure, function and biochemistry is so called spatial frequency domain imaging (SFDI). This is a modulated illumination technique wherein a spatial frequency is used for imaging a sinusoid or other repetitive shape on tissue, for example, by means of a spatial light modulator or digital mirror device. SFDI has typically been used in geometries where large areas of tissue can be exposed, such as skin. The retina is a very thin curved tissue with a water/tissue refractive index interface offering limited optical access to measure optical characteristics. For retinal imaging SFDI, is considered not useful due to its low spatial resolution, large imaging depth that significantly extends beyond the retina, and small size of the retina compared to the spatial frequencies usually employed for SFDI (typically 0-0.2 mm$^{-1}$, or 0-0.33$\mu_{tr}$, where 1/$\mu_{tr}$ is the transport mean free path).

From US20160157723 a technique called sub diffuse spatial frequency imaging is known (sd-SFDI). sd-SFDI has shown promise in quantifying the subdiffuse scattering properties of easily accessible turbid media such as skin. However, the water-tissue interface of the retina; the curvature of the retina and the maximum projectable extent of the patterned illumination in the retina vs. skin are not comparable with the flat geometry of air-tissue interface. Furthermore, US20160157723 shows quantification of the absorption properties of easily accessible turbid media using spatial frequencies usually employed for SFDI, which are not appropriate for imaging the absorption properties of the retina. The invention has as an object to provide an imaging technique that does not suffer from the afore described problems and that is able to provide an enhanced, quantitative image of the retina.

SUMMARY OF THE INVENTION

This can be done by a method and system for imaging the retinal structure of an eye according to the referenced claims. A light source is provided and a repetitive pattern is projected on the retina by said light source having illuminated and non-illuminated portions with a spatial frequency larger than 0.33$\mu_{tr}$. The periodic signal is shifted in phase and the phase-shifted images are combined to form a demodulated image, for which a tissue optical transport model is used to determine the tissue optical properties. A high spatial frequency of the phase shifted images induces an additional sensitivity to the angular scattering distribution related to sub-diffuse light transport. In an embodiment, a fluorescence level is measured; and a fluorescence level is derived as a corrected value for the effects of optical properties on measured fluorescence level, thereby allowing measurement of undistorted, intrinsic fluorescence and distinguishing autofluorescence from labeled fluorescence.

By projecting the phase shifted images with spatial frequencies in a sub-diffuse region, such high spatial frequencies are utilized as a wide-field equivalent of spatially resolved diffuse reflectance measurements at short source-detector separations. This sub diffuse technique has the following advantages for obtaining an optical characteristic of the retina. The limited penetration depth of the sub-diffuse light that is required due to the small thickness of the retina, enables to accurately recover optical property maps of the retina without any distorting effects from the underlying choroid. Second, the spatial frequencies employed (>0.33$\mu_{tr}$) are useful in the limited-area geometry of the retina, which has a typical retinal image sizes of about 15 mm in diameter. It is noted that $\mu_{tr}$ is the transport coefficient, which is the sum of an absorption coefficient $\mu_a$ and a reduced scattering coefficient $\mu'_s$ measured in mm$^{-1}$. In addition, implementation of the projection technique in the retina is particularly advantageous since specular reflections that are problematic for current application areas are not present in the retina due to a combination of annular illumination (or other optical solutions) used in fundus camera's to reduce the corneal reflections, and the relatively small specular reflectance of the retina due to the small vitreous-retina refractive index mismatch.

In US2016/0157723 A1 a structured light imaging method is described to measure sub-diffuse scattering parameters, being reduced scattering coefficient and backscatter likelihood. It is the objective of the current invention to measure sub-diffuse scattering, absorption and fluorescence parameters in the thin top-layer of a 2-layer medium, i.e. the retina on top of the choroid. Although in US2016/0157723 A1 it is understood that absorption and fluorescence of a material can be measured using SFDI, it is suggested to do so with low spatial frequency modulated patterns which is not appropriate for separating retinal absorption and fluorescence from choroid absorption and fluorescence.

DETAILED DESCRIPTION OF THE DRAWINGS

Figure 1:
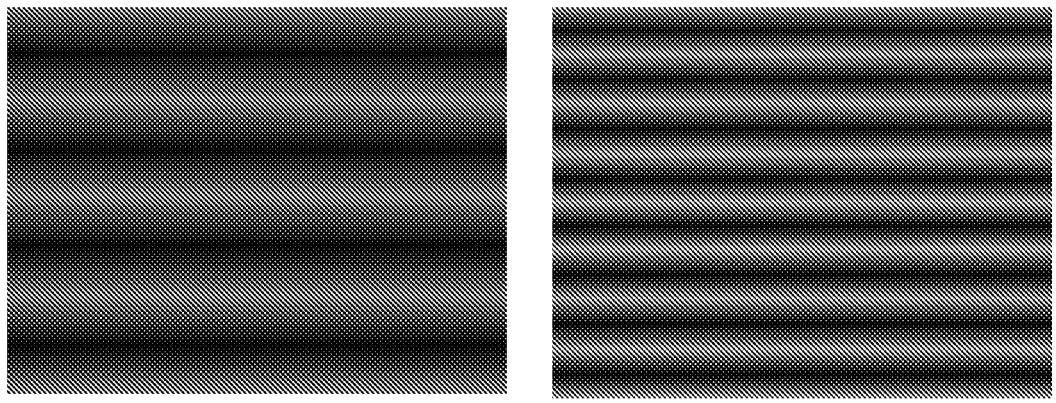
FIG. 1 shows an example of spatially varying patterns that can be projected onto the retina.

There has been significant success in performing quantitative fiber-optic probe measurements during clinical procedures to quantify sub-diffuse scattering, absorption and fluorescence in small tissue volumes outside the eye. This single-point contact approach of contact fibers is however not compatible with wide-field retinal imaging.

Current state-of-the-art retinal imaging devices are unable to relate collected images to the retinal tissue optical properties (scattering and absorption). When light enters tissue it is scattered due to fluctuations in the optical refractive index related to tissue structure, and it is absorbed due to the presence of chromophores such as bilirubin, carotenoids and hemoglobin. Quantification of these scattering and absorption properties of tissue is likely to be diagnostically valuable, as changes in light scattering can be directly correlated to changes in tissue microstructure while changes in absorption can be directly correlated to changes in pigmentation, bilirubin/carotenoid concentration and vascular properties such as microvascular blood oxygenation.

Moreover, differences in tissue optical properties have been shown to have a strong influence on the amount of fluorescence signal that is collected under wide-field optical imaging. Unless these differences are appropriately corrected for, this can lead to misinterpretation of fluorescence molecular imaging signatures. This can be overcome by measuring the tissue optical properties and using this knowledge e.g. to correct the raw fluorescence to recover the intrinsic, undistorted fluorescence from naturally present fluorophores such as lipofuscin or from labeled fluorophores such as curcumin or targeted fluorescent tracers such as Bevacizumab-IRDye800CW.

In further embodiments, the retinal image is spectrally analysed. Spectral analysis of the sub-diffuse scattering and absorption properties is particularly advantageous for accurate determination of molecular concentrations of absorbing and fluorescent molecules through spectral unmixing, as is known from the prior art. In another embodiment a scattering coefficient $\mu_s$ is measured as average number of scattering events per unit distance [mm$^{-1}$]. Also a phase function $p(\Theta)$ is measured as an angular scattering distribution of tissue.

For spatial frequency responses two regimes exist in tissue, without a clear regime boundary. But for patterns with a pitch smaller than $3/\mu_{rr}$, i.e. a spatial frequency larger than $0.33\mu_{rr}$, a sub diffuse regime has a smaller interrogation depth and provides more information on scattering since phase information remains preserved, in contrast to the diffuse region. This is a critical aspect of imaging the retina, wherein the retina including its blood saturation level and vascular structure must be discriminated from the underlying choroid. These values are of significant importance for analyzing the tissue structure and function of the retina, since accordingly one can determine absolute absorbance values indicative of the presence of (molecular concentrations of) certain chromophores and fluorophores.

FIG. 1 shows an example of spatially varying patterns that can be projected onto the retina. For example, a sinusoid pattern can be provided at a certain pitch, e.g. 2 mm, for a first spectral wavelength, e.g. in the 450-600 nm range. In the following, the spectral spreading can be very small, e.g. less than 1 nm, or can be larger, eg. 50 nm.

For another wavelength, e.g. 700 nm, another pitch can be used, e.g. of 1.7 mm. In this way, overlapping patterns of different colors can be projected simultaneously at different pitches, which can be deconvoluted by applying a Fourier transform as is known from the prior art. By providing a repetitive pattern for a plurality of spectral bands, each having its own spatial frequency, simultaneous projection of such repetitive patterns is possible, that can be detected independently. In this way, increasing the spectral resolution will not go to the detriment of the camera's framerate.

The patterns are spatially varying, and can be temporally varying as well, for instance, for a scanning sinusoid pattern that is moved over the retina. Alternatively a scanning point source, or scanning patterns of various dimensions in the form of circles lines or ellipses can be provided.

Figure 2:
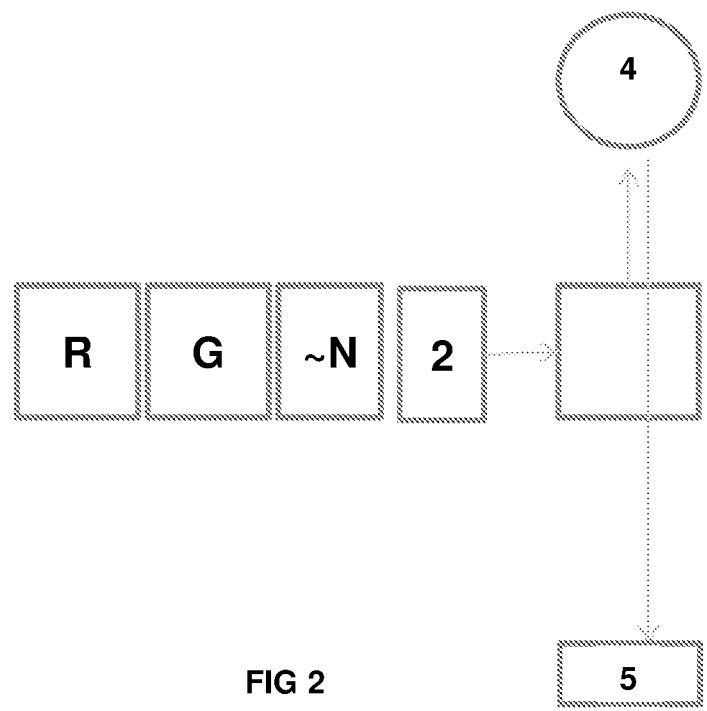
FIG. 2 shows a configuration of a narrow banded n-color source.

FIG. 2 shows a configuration of a narrow banded n-color source, e.g. RGB source. In the Fourier plane of a lens system (not depicted), a high frequency spatial light modulator 2 is arranged, that is able to project n-numbered patterns, e.g. a blue pattern, red pattern and green pattern, as depicted in FIG. 1.

Figure 3:
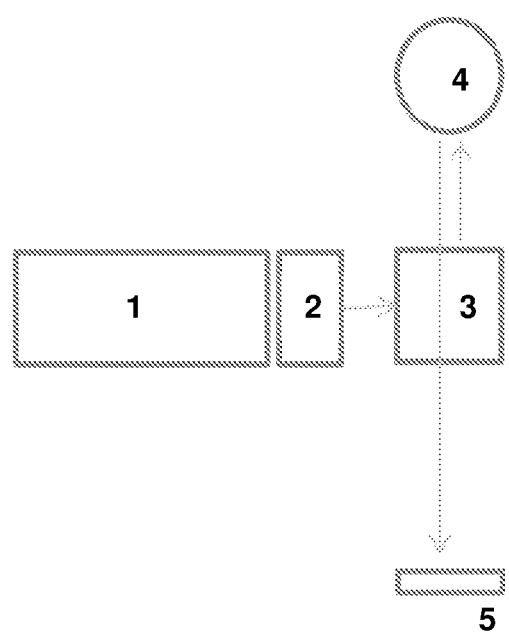
FIG. 3 shows a configuration of the broad band light source

FIG. 3 shows a configuration of the broad band light source 1, that is capable of projecting various patterns, via a spatial light modulator 2 and a dichroic mirror 3, to the eye 4. Such patterns can be provided by projecting said repetitive pattern by a scanning light beam from said light source derived from a DMD or SLM and using a photodiode or camera 5 as an optical detector. The detector 5 is capable of registering light from the illuminated pattern on the retina, as well as light from neighbouring parts. This light contains information on the tissue through which it travelled. The detector may be multispectral, divided over several channels. In this way simultaneous spectral detection of several wavelengths is feasible. The application of a multispectral camera that images a large number of spectral bands at the expense of a low spatial resolution, by e.g. creating a mosaic pattern of pixel-based color filters on the imaging chip, is appropriate for sd-SFDI since the spatial resolution achieved by sd-SFDI is fundamentally limited by the tissue light transport properties anyway, allowing to use a large number of imaging wavelengths at the expense of a low spatial pixel resolution on the imaging chip. The camera can also be a monochrome camera, providing an instantaneous multispectral image, without necessarily projecting multiple colors sequentially.

By flash projection or continuous illumination, an optical response of for example biomarkers in the retina can be influenced.

The invention is not limited to the projection of patterned images, but can be used with other techniques as well, such as Raman scattering, 2 photon fluorescence lifetime measurement. In addition, instead of a (pinhole) camera a photodiode array can be used to provide a detection similar to scanning laser ophthalmoscopy (SLO). A difference with regular SLO is that here information on the scatter path is used (via scattering and absorption). Annular projection in combination with a polarizing filter may prevent specular reflection in the air-lens surface or in the pupil. Variations are a full illumination of the pupil, a halve illumination, ring illumination or point illumination. These variations will alter the optical transfer path through the retina to the camera.

An example of an optical transport model is given as follows:

$$R_{SF}^{Model}(\mu_a, \mu_s', \gamma, d_{fib}, NA, n_{medium}) =$$

$$\frac{NA^2}{n_{medium}^2}\left(1 + 0.62\gamma^2 e^{-2.3\gamma^2(\mu_2 d_{fib})}\right)\left[\frac{(\mu_s' d_{fib})^{0.57\gamma}}{2.3\gamma^2 + (\mu_s' d_{fib})^{0.57\gamma}}\right]$$

$$e^{-\mu_a}\frac{1.05_\gamma^{0.6} d_{fib}}{(\mu_s' d_{fib})^{0.18}(0.64 - (\mu_a d_{fib})^{0.64})}$$

In a preferred embodiment, the retina is illuminated with spatial patterns of the form:

$$S = \frac{S_0}{2}[1 + M_0 \cos(2\pi f_x x + \alpha)]$$

where $S_0$, $M_0$, $f_x$, and $\alpha$ (alpha) are the illumination source intensity, modulation depth, spatial frequency, and spatial phase, respectively. In this simple case, the pattern is constant in the orthogonal y direction. In reflection mode, the sub-diffusely reflected intensity, I, is a sum of AC and DC components, $I = I_{AC} + I_{DC}$, where the measured AC component of the reflected intensity, $I_{AC}$, can be modeled as:

$$I_{AC} = M_{AC}(x, f_x) \cdot \cos(2\pi f_x x + \alpha).$$

Here, $M_{AC}(x, fx)$ represents the amplitude envelope of the reflected photon density standing wave at frequency $f_x$. Note that multiple $M_{AC}(x, f_x)$ curves can be sampled in parallel at each y pixel row using a 2-D camera, allowing spatial sampling of millions of reflectance values simultaneously.

It is known from the prior art to employ a simple time-domain amplitude demodulation method, illuminating a sinusoid pattern three times at the same spatial frequency, with phase offsets $\alpha=0$, $\frac{2}{3}\pi 1$, and $\frac{4}{3}\pi$ radians. $M_{AC}(x, f_x)$ can then be calculated algebraically at each spatial location, $x_i$, by:

$$M_{AC}(x_i, f_x) = \frac{2^{1/2}}{3}\{[I_1(x_i) - I_2(x_i)]^2 + [I_2(x_i) - I_3(x_i)]^2 + [I_3(x_i) - I_1(x_i)]^2\}^{1/2},$$

where $I_1$, $I_2$, and $I_3$ represent the LC image values at each location with shifted spatial phases. This differencing approach is convenient, as it automatically removes features common to all three images, including the average image noise and digitization offset.

The spatially varying DC amplitude, $M_{DC}(x_i)$, can be calculated as earlier with $f_x=0$, or at any frequency of illumination using:

$$M_{DC}(x_i) = \frac{1}{3}[I_1(x_i) + I_2(x_i) + I_3(x_i)]$$

In the frequency domain, a measurement $M_{AC}(x, f_x)$ is the product of the source intensity, $I_0$; the modulation transfer function (MTF) of the illumination and imaging optical system, $MTF_{system}$; and the true turbid system MTF, $R_d(x_i, f_x)$:

$$M_{AC}(x_i, f_x) = I_0 \cdot MTF_{system}(x_i, f_x) \cdot R_d(x_i, f_x)$$

Therefore, we can simultaneously calibrate for the absolute intensity of the source and the MTF of the imaging system by performing a reference measurement, $M_{AC,ref}(x, f_x)$, on a turbid phantom of known optical properties. Using a model prediction for the phantom diffuse reflectance, $R_{d,ref,pred}(f_x)$, we can write the sub-diffuse reflectance at each spatial location as:

$$R_d(x_i, f_x) = \frac{M_{AC}(x_i, f_x)}{M_{AC,ref}(x_i, f_x)} \cdot R_{d,ref,pred}(f_x).$$

This direct division-based correction for the system frequency response is an advantage of SFD measurement over other spatially resolved measurements, avoiding system PSF deconvolution in the real spatial domain, which can amplify measurement noise and uncertainties. Ideally, the surface contours of the sample and the phantom should be identical or be compensated numerically using surface profilometry. Note that in sub-diffuse imaging, the exact phase function of the calibration phantom must be known in order to correctly calculate $R_{d,ref,pred}(f_x)$.

In a preferred embodiment, multiple spatial frequencies will be used and multiple wavelengths will be used in order to obtain sufficient information to fit the data $R_d(x_i, f_x)$ to a reflectance model that describes the dependence of the signal $R_d(x_i, f_x)$ on the tissue optical properties $\mu_s'$, y, and $\mu_a$. As an initial guess, the reflectance model dependence on scattering properties $\mu_s'$ and $\Gamma$ is based on the idea that $R_d$ exhibits a Y-specific proportionality vs. dimensionless scattering given as the product of ($\mu_s' f_x^{-1}$):

$$R_d(\mu_s', \gamma, f_x) = \eta\left(1 + (\zeta_4\gamma^{-2})(\mu_s'f_x^{-1})^{(-\zeta_3\gamma)}\right)\left[\frac{(\mu_s'f_x^{-1})^{(-\zeta_2\gamma)}}{\zeta_1\gamma^2 + (\mu_s'f_x^{-1})^{(-\zeta_2\gamma)}}\right] \quad (1)$$

Here the fitted parameters include n, which represents the collection efficiency of the detector, and, for $\zeta_i$, for i=[1,2,3,4], which are fitted coefficients used to capture the dynamics in demodulated reflectance observed in response to changes in $\mu_s' f_x^{-1}$ and Y. Note that equation (1) is the wide-field non-contact equivalent of reflectance collected with a single fiber in contact with tissue. Model coefficients can be estimated by minimizing the difference between simulated and model estimated values of demodulated reflectance. Monte Carlo simulations of light transport can be used, using the repetitive patterns that are projected onto the retinal tissue, which is a curved turbid medium, to derive the map of retinal optical properties, including the absorption coefficient $\mu_a$ and a reduced scattering coefficient $\mu_s'$ measured in $mm^{-1}$.

The effect of absorption on remitted reflectance can also be specified for sd-SFDI. As an initial guess, the model structure follows from expressions for effective photon path length in the sub-diffuse single fiber reflectance geometry, $$R_d(f_x, \mu_s', \gamma, \mu_a) = R_d(f_x, \mu_s', \gamma)e^{-\mu_a \langle L \rangle} \quad (2)$$

$$\langle L \rangle = f_x^{-1} \frac{p_1 C_{PF}}{(\mu_s' f_x^{-1})^{p_2}(p_3 + (\mu_a f_x^{-1})^{p_3})} \quad (3)$$

Here $C_{PF}$ and $p_1$-$p_3$ are fitted coefficients used to capture the dynamics in attenuation of demodulated reflectance observed in response to changes in $\mu_s'$, $f_x^{-1}$, $\gamma$ and $\mu_a$. Model coefficients can be estimated by minimizing the difference between simulated and model estimated values of demodulated reflectance. Other expressions than Eq. (2,3) may also be investigated to describe the effect of attenuation due to absorbing molecules on the collected signals.

The invention claimed is:

1. A non-invasive method of obtaining an image of a curved retina structure of an eye by sub-diffuse spatial frequency retinal imaging, the method comprising:
   providing a light source;
   projecting a light in a plurality of phase shifted repetitive patterns on the curved retina structure by said light source, each pattern, of the plurality of phase shifted repetitive patterns, having an illuminated portion and a non-illuminated portion with a spatial frequency larger than $0.33\mu_{tr}[\mathrm{mm}^{-1}]$;
   measuring, for each pattern of the plurality of phase shifted repetitive patterns on the curved retina structure, an optical response for the illuminated portion and the non-illuminated portion of the curved retina structure; and
   deriving a retina tissue absorption value by combining, for each pattern of the plurality of phase shifted repetitive patterns on the curved retina structure, the optical response for the illuminated portion and the non-illuminated portion of the curved retina structure.

2. The method according to claim 1 wherein said light in a plurality of phase shifted repetitive patterns is simultaneously provided for a plurality of spectral bands, and wherein each one of the plurality of spectral bands has a distinct spatial frequency.

3. The method according to claim 1 wherein, for the illuminated and the non-illuminated portions, a tissue optical transport model is used for determining at least one of the group consisting of: the retina tissue absorption value, a retina tissue scattering value, and a retina tissue fluorescence value.

4. The method according to claim 1, further comprising:
   measuring a fluorescence level, and
   deriving, in accordance with the measuring a fluorescence level, a real fluorescence level for the illuminated portion and the non-illuminated portion.

5. The method according to claim 1, wherein the projecting a plurality of phase shifted repetitive patterns is carried out by a scanning light beam from said light source derived from a digital micro-mirror device (DMD) or a spatial light modulator (SLM), and
   wherein the measuring is carried out using a photodiode or camera as an optical detector.

6. The method according to claim 1, wherein the plurality of phase shifted patterns are one or more of the group consisting of: a sinusoidal patterns, a line patterns, a dot patterns, and a concentric patterns.

7. The method according to claim 1, wherein a scattering coefficient $\mu_s$ is measured as an average number of scattering events per unit distance.

8. The method according to claim 1, wherein, during the measuring, a phase function is measured as an angular scattering distribution of a tissue.

9. The method according to claim 1, wherein the method further comprises spectrally analyzing the image for one or more chromophores taken from the group consisting of: an oxygenated hemoglobin, a deoxygenated hemoglobin, a melanin, a bilirubin, a beta-carotene, a lipid, and water.

10. A non-invasive retinal imaging system for imaging a curved retina structure of an eye by sub-diffuse spatial frequency retinal imaging, the system comprising:
    a light source;
    a projector that projects a light of the light source in a plurality of phase shifted repetitive patterns on the curved retina structure, each pattern, of the plurality of phase shifted repetitive patterns, having an illuminated portion and a non-illuminated portion with a spatial frequency larger than $0.33\ \mu_{tr}[\mathrm{mm}^{-1}]$;
    an optical detector that detects, for each pattern of the plurality of phase shifted repetitive patterns on the curved retina structure, an optical response for the illuminated portion and the non-illuminated portion of the curved retina structure; and
    a processing device that derives a retina tissue absorption value by combining, for each pattern of the plurality of phase shifted repetitive patterns on the curved retina structure, the optical response for the illuminated portion and the non-illuminated portion of the curved retina structure.

11. The system according to claim 10 wherein said light in a plurality of phase shifted repetitive patterns is simultaneously provided for a plurality of spectral bands, and wherein each one of the plurality of spectral bands has a distinct spatial frequency.

12. The system according to claim 10 wherein, for the illuminated and the non-illuminated portions, a tissue optical transport model is used for determining at least one of the group consisting of: the retina tissue absorption value, a retina tissue scattering value, and a retina tissue fluorescence value.

13. The system according to claim 10, further comprising:
    measuring a fluorescence level, and
    deriving, in accordance with the measuring a fluorescence level, a real fluorescence level for the illuminated portion and the non-illuminated portion.

14. The system according to claim 10, wherein a projecting, by the projector, the plurality of phase shifted repetitive patterns is carried out by a scanning light beam from said light source derived from a digital micro-mirror device (DMD) or a spatial light modulator (SLM), and
    wherein a measuring, by the optical detector, the optical response is carried out using a photodiode or camera as an optical detector.

15. The system according to claim 10, wherein the plurality of phase shifted patterns are one or more of the group consisting of: a sinusoidal patterns, a line patterns, a dot patterns, and a concentric patterns.

16. The system according to claim 10, wherein a scattering coefficient $\mu_s$ is measured as an average number of scattering events per unit distance.

17. The system according to claim 10, wherein, during a detecting by the optical detector, a phase function is measured as an angular scattering distribution of a tissue.

18. The system according to claim 10, wherein the processing device is configured to spectrally analyze the image for one or more chromophores taken from the group consisting of: an oxygenated hemoglobin, a deoxygenated hemoglobin, a melanin, a bilirubin, a beta-carotene, a lipid, and water.

19. The system of claim 10, wherein each illumination is provided by light having a spectral band overlapping with an absorption property of retinal tissue of the eye.

20. The method of claim 1, wherein each illumination is provided by light having a spectral band overlapping with an absorption property of retinal tissue of the eye.

* * * * *